United States Patent
Kørsgaard

(10) Patent No.: US 6,328,685 B1
(45) Date of Patent: Dec. 11, 2001

(54) MAGNETICALLY THERAPEUTIC TREATMENT DEVICE

(76) Inventor: Børge Kørsgaard, Torning-Møllevej 9, Christiansfeld 6070 (DK)

( * ) Notice: Subject to any disclaimer, the term of this patent is extended or adjusted under 35 U.S.C. 154(b) by 0 days.

(21) Appl. No.: 09/529,196

(22) PCT Filed: Sep. 23, 1998

(86) PCT No.: PCT/DK98/00413

§ 371 Date: Apr. 7, 2000

§ 102(e) Date: Apr. 7, 2000

(87) PCT Pub. No.: WO99/20344

PCT Pub. Date: Apr. 29, 1999

(30) Foreign Application Priority Data

Oct. 16, 1997 (DK) .............................................. 9700387 U

(51) Int. Cl.[7] .................................................... A61N 2/08
(52) U.S. Cl. .................................................. 600/9; 600/15
(58) Field of Search ........................... 600/9, 15; 372/23; 607/1; 435/7.21

(56) References Cited

U.S. PATENT DOCUMENTS 5,827,170 * 10/1998 Gebran .................................... 600/15

FOREIGN PATENT DOCUMENTS

| 29621571-U1 | * | 5/1997 | (DE) | ................................ | A61N/2/08 |
| 0712620-A1 | * | 5/1996 | (EP) | ................................ | A61H/39/04 |
| 7-275019-A | * | 10/1995 | (JP) | ................................ | A61N/1/42 |

* cited by examiner

Primary Examiner—Eric F. Winakur
Assistant Examiner—Nikita R Veniaminov
(74) Attorney, Agent, or Firm—Merchant & Gould P.C.

(57) ABSTRACT

The present invention relates to a magnetically therapeutic treatment device for treatment of biological tissue for the acceleration of a heating process in a damaged or in other ways diseased body area by the use of a magnetic device for providing a magnetic field in the immediate vicinity of said body area by the movement of a crystal member immediately above the magnetic device, wherein a group of magnetic devices are annually arranged in a magnet fixture, where the magnetic devices are equally distributed on a support plate, over which one or more crystals are rotatably arranged in a crystal holder that is connected to rotation means for rotation in a relative to the arrangement of the magnetic devices concentric motion. By the use of a magnetic therapeutic treatment device according to the invention, a treatment of an area of the body can be performed without the aid of a helping assistant. This in turn means that areas that so far in practice have been impossible to treat are now reachable with a magnetically therapeutic treatment device according to the invention.

4 Claims, 3 Drawing Sheets

FIG.1
FIG.2
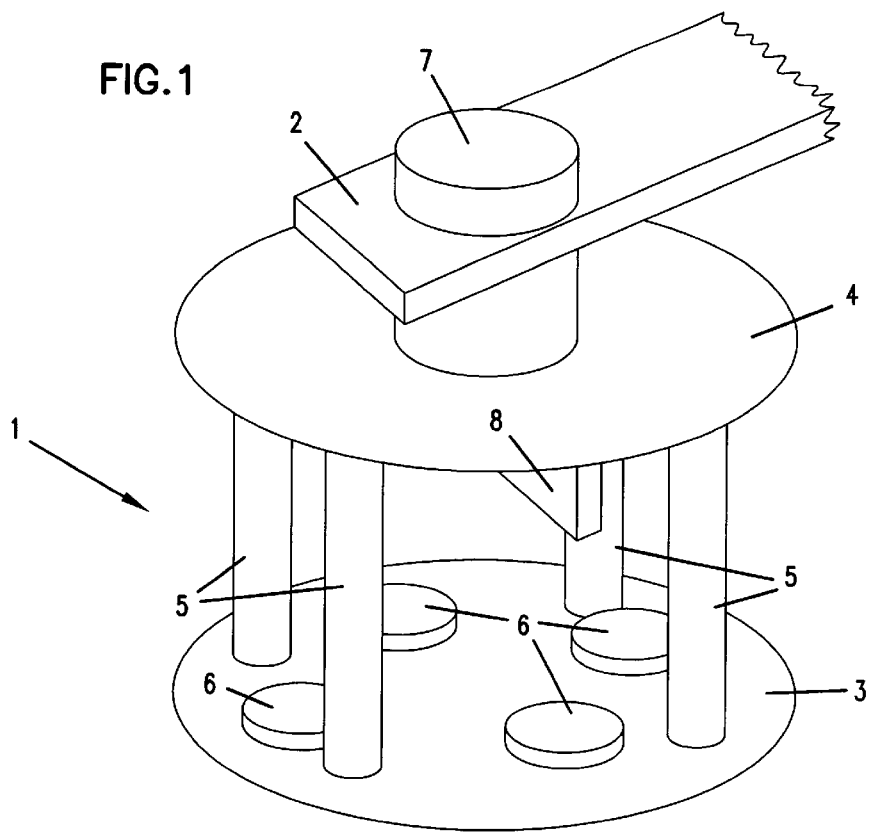
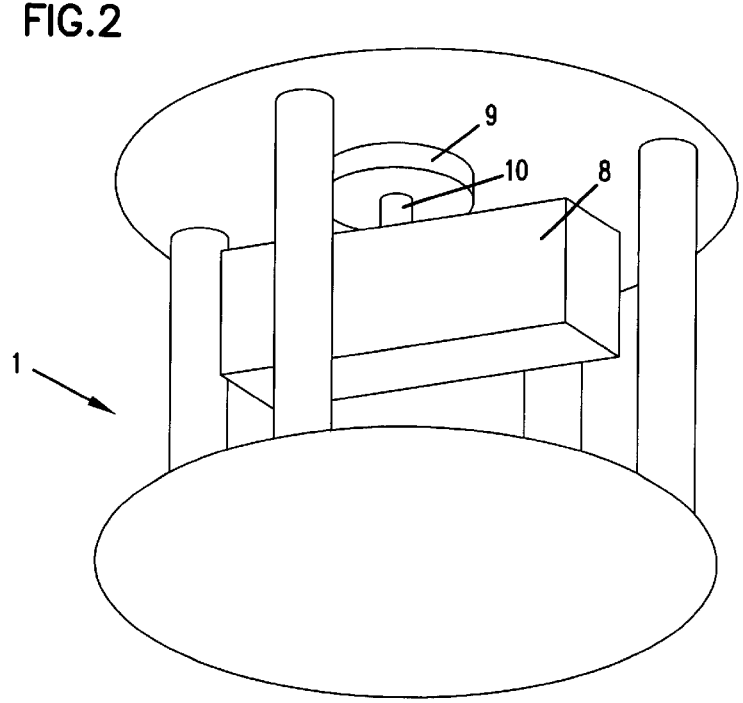

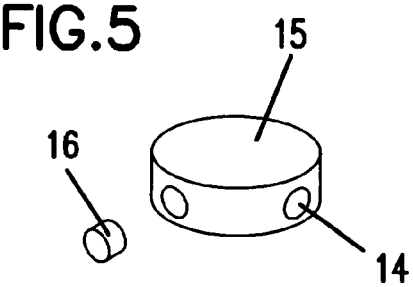
FIG.5
FIG.6
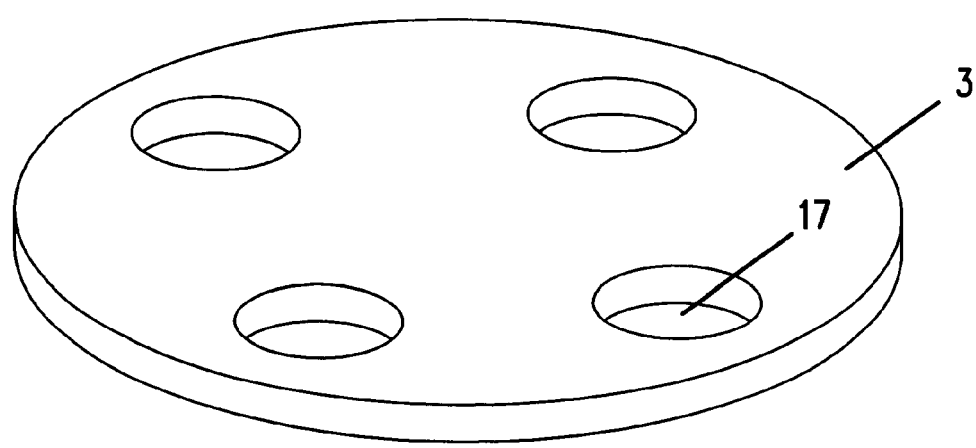

MAGNETICALLY THERAPEUTIC TREATMENT DEVICE

The present invention relates to a magnetically therapeutic treatment device for treatment of biological tissue for the acceleration of a healing process in a damaged or in other ways diseased body area by the use of a magnetic device for providing a magnetic field in the immediate vicinity of said body area by the movement of a crystal member immediately above the magnetic device.

BACKGROUND OF THE INVENTION

A treatment device of such kind is known from the Danish utility model No. 95 00474 and the German utility model No. 296 21 571.6 where a magnetic device is placed adjacent to the body area that is to be treated, with a crystal is moved in smooth motions above the magnet by the therapist, an assistant or the patient himself.

This known magnetically therapeutic treatment device with crystals is inconvenient in practical use, since it is only possible to work with a few pieces at the time and because it can prove difficult to maintain the magnet and the crystal in a regular, uniform motion of movement over a period of time. Moreover, only a shorter duration of the treatment is available by this device as, in particular the crystal movements are particularly exhausting to perform over a longer period of time for the manipulator.

SUMMARY OF THE INVENTION

Moreover, many treatments are difficult to carry out by the patient alone. Hence, a therapist or an assistant is often needed in order to perform the treatment.

With this background it is the object of the invention to provide a magnetically therapeutic treatment device that overcomes the above mentioned drawbacks by the known devices of this kind.

The invention consists of a magnetically therapeutic treatment device of the initially mentioned kind, where a group of magnetic devices are annularly arranged in a magnet fixture, where the magnetic devices are equally distributed on a support plate, over which one or more crystals are rotatably arranged in a crystal holder that is connected to rotation means for rotation in a relative to the arrangement of the magnetic devices concentric motion.

By the use of a magnetic therapeutic treatment device according to the invention, a treatment of an area of the body can be performed without the aid of a helping assistant. This is turn means that areas that so far in practice have been impossible to treat are now reachable with a magnetically therapeutic treatment device according to the invention. Moreover, with the automatically rotating crystals it is possible to perform a treatment of a relatively long duration that up until now has not been possible in practise. In addition, the process of the treatment can easily be described and be reported since it is encompassed in the design of the magnetic device in the actual case.

BRIEF DESCRIPTION OF THE SEVERAL VIEWS OF THE DRAWINGS

The invention will be described more detail below with reference to the accompanying drawings, in which FIG. 1 is a perspective view from above of a magnetic fixture, FIG. 2 is a perspective view from below of a magnetic fixture, FIG. 5 shows a magnetic device, and FIG. 6 shows a support plate for the mounting of magnetic devices in a concentric annular configuration.

DETAILED DESCRIPTION OF THE INVENTION

Figure 3:
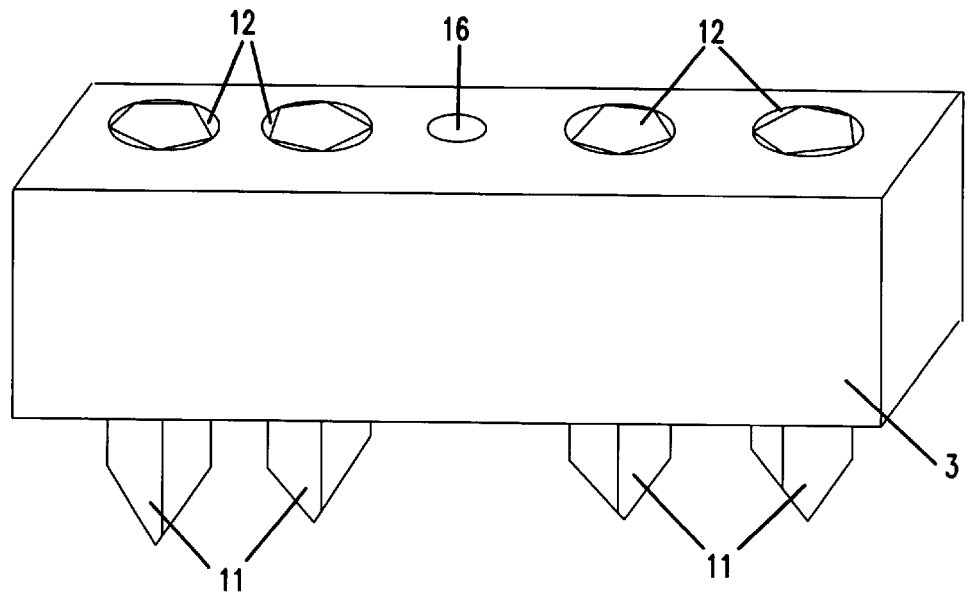
FIG. 3 shows a crystal holder with an arrangement of crystals.

FIG. 1 shows a magnet fixture 1 with a holder 2. The magnet fixture comprises a support plate 3, a top plate 4 and a number of distance pieces 5. On the support plate 3 a number of magnetic devices 6 are placed in a determined pattern, preferably in a circle. The magnetic devices 6 are preferably disc shaped with a number of permanent magnets radially arranged in such a way that they are directed with alternatively a north and south pole towards the center of the disc. The magnet fixture 1 comprises furthermore a cover 7 for suspending it in the holder 2. Under the cover 7 the device 1 is provided with a motor 9 that is connected to the crystal holder 8 with an axle 10, see FIGS. 2 and 3. The motor 9 is preferably controlled by a timer o that the time of treatment can be determined in advance and the motor automatically cuts out when the determined time of treatment is up.

FIG. 2 shows a magnet fixture seen from below with the support plate 3 and the top plate 4. Furthermore, the crystal holder 8 is displayed and the motor 9 and the axle 10 that connects the motor 9 and the crystal holder 8.

The crystal holder is shown in FIG. 3 with a number of crystals 11 arranged according to the first embodiment. The number of crystals, and also the type, size, form and colour of the crystals can be chosen individually. In the preferred embodiment, the crystals 11 are placed in suitable recesses 12. Other kinds of fixations can naturally also be used, such as elastic holders, for any easy replacement, demounting or insertion of crystals according to the actual need. The crystal holder 8 preferably in its central line of symmetry provided with a hole 16 for the reception of the motor axle 10.

Figure 4:
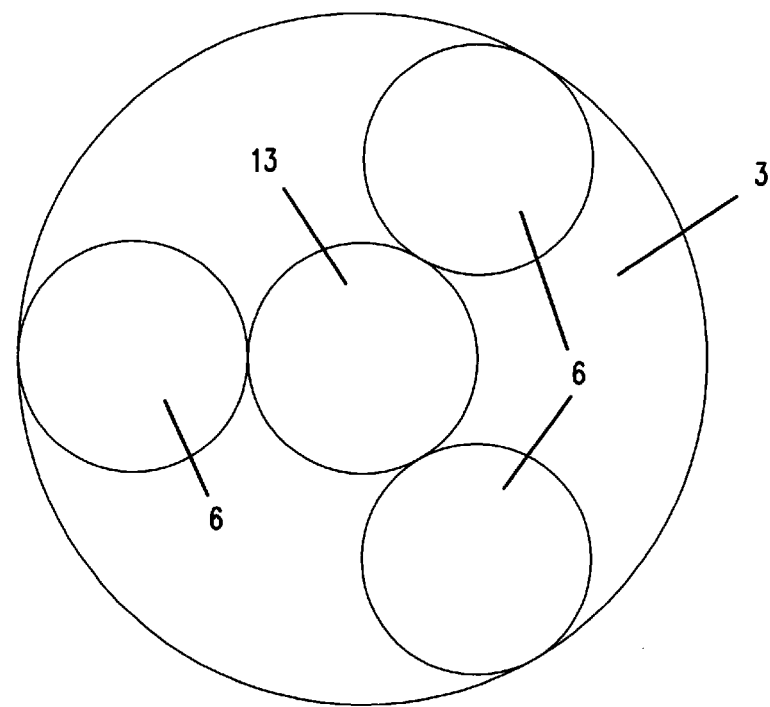
FIG. 4 shows an arrangement for the installation of magnetic devices on a support plate.

FIG. 4 shows a loose magnet plate 3 with a number of disc-shaped magnet devices 6. The can placed in recesses 17 (see FIG. 6) and said plate is suitably placed on the support plate 3. the magnets 6 are here provided with external gearing tooths (not shown) that are intermeshing with a central gearing wheel 13. Outmost, the magnet plate 3 is provided with a gearing or alternatively a number of gearing wheels could be arranged between the magnets 6. A motor drives one of the gearing wheels 13.

FIG. 5 shows an embodiment of the magnet device 6 where the magnets 16 are inserted in holes 14 that are shaped like discs 15 and put down on the support plate 3 in the recesses 17 therein, as shown in FIG. 6.

What is claimed is:

1. A magnetically therapeutic treatment device for treatment of biological tissue for the acceleration of a healing process in a damaged or in other ways diseased body area by the use of a magnetic device for providing a magnetic field in the immediate vicinity of said body area by the movement of a crystal member immediately above the magnetic device comprising a group of magnetic devices anuallarly arranged in a magnetic fixture, where the magnetic devices are equally distributed on a support plate, over which one or more crystals are rotatably arranged in a crystal holder that is connected to rotation means for rotation in a concentric motion relative to the arrangement of the magnetic devices.

2. A magnetically therapeutic treatment device according to claim 1, wherein the angular velocity and direction of the rotation of the crystal holder is variable.

3. A magnetically therapeutic treatment device according to claim 1, wherein each of the magnetic devices is disk shaped, and consists of radial directed permanent magnets with alternately the magnetic north and magnetic south end towards the center of the magnetic device.

4. A magnetically therapeutic treatment device according to claim 1, wherein the treatment device is suspended in a holder that comprises one or more swivel joints in order to position the treatment device relative to the body area to be treated.

\* \* \* \* \*

UNITED STATES PATENT AND TRADEMARK OFFICE
CERTIFICATE OF CORRECTION

PATENT NO. : 6,328,685 B1
DATED : December 11, 2001
INVENTOR(S) : Kærsgaard

It is certified that error appears in the above-identified patent and that said Letters Patent is hereby corrected as shown below:

<u>Title page,</u>
Item [76], inventor, "Børge Kørsgaard" should read -- Børge Kærsgaard --

Signed and Sealed this

Twenty-fifth Day of June, 2002

Attest:

JAMES E. ROGAN
Attesting Officer　　　　　　　　　Director of the United States Patent and Trademark Office